(12) United States Patent
Freitag et al.

(10) Patent No.: US 9,150,711 B2
(45) Date of Patent: Oct. 6, 2015

(54) FLAME RETARDANT POLYAMIDE COMPOSITIONS

(71) Applicant: FRX POLYMERS, INC., Chelmsford, MA (US)

(72) Inventors: Dieter Freitag, Krefeld (DE); Pin Go, Lowell, MA (US); Youmi Jeong, Boxborough, MA (US); Lawino Kagumba, Cambridge, MA (US)

(73) Assignee: FRX Polymers, Inc., Chelmsford, MA (US)

( * ) Notice: Subject to any disclaimer, the term of this patent is extended or adjusted under 35 U.S.C. 154(b) by 61 days.

(21) Appl. No.: 13/674,529

(22) Filed: Nov. 12, 2012

(65) Prior Publication Data

US 2013/0123402 A1 May 16, 2013

Related U.S. Application Data

(60) Provisional application No. 61/558,296, filed on Nov. 10, 2011.

(51) Int. Cl.

| | |
|---|---|
| *C08L 77/00* | (2006.01) |
| *C08K 5/5399* | (2006.01) |
| *C07F 9/44* | (2006.01) |
| *C08G 79/02* | (2006.01) |
| *C08G 69/40* | (2006.01) |
| *C08L 77/02* | (2006.01) |
| *C08L 77/06* | (2006.01) |
| *C08L 85/02* | (2006.01) |

(52) U.S. Cl.
CPC ............ *C08K 5/5399* (2013.01); *C07F 9/4465* (2013.01); *C07F 9/4476* (2013.01); *C08G 69/40* (2013.01); *C08G 79/02* (2013.01); *C08L 77/00* (2013.01); *C08L 77/02* (2013.01); *C08L 77/06* (2013.01); *C08L 85/02* (2013.01)

(58) Field of Classification Search
CPC ............................. C09K 5/5399; C07F 9/4465
USPC ........................................................ 524/121
See application file for complete search history.

(56) References Cited

U.S. PATENT DOCUMENTS

| | | |
|---|---|---|
| 3,635,910 A | 1/1972 | Sills et al. |
| 4,403,075 A | 9/1983 | Byrd et al. |
| 4,701,554 A | 10/1987 | Kauth et al. |
| 5,326,850 A * | 7/1994 | Goetz et al. ................... 528/345 |
| 6,221,939 B1 | 4/2001 | Campbell et al. |
| 6,291,700 B1 | 9/2001 | Cella et al. |
| 7,888,534 B2 | 2/2011 | Freitag et al. |
| 7,928,259 B2 | 4/2011 | Freitag et al. |
| 2007/0149663 A1* | 6/2007 | Schmidt et al. ............... 524/227 |

FOREIGN PATENT DOCUMENTS

| | | |
|---|---|---|
| JP | 2001-139823 A | 5/2001 |
| WO | WO-2012065098 A2 | 5/2012 |

OTHER PUBLICATIONS

International Search Report dated Mar. 27, 2013 of corresponding application PCT/US2012/064664.
Supplementary European Search Report dated Apr. 29, 2015 for European Patent Application No. EP12847309.

\* cited by examiner

*Primary Examiner* — Doris Lee
(74) *Attorney, Agent, or Firm* — Pepper Hamilton LLP

(57) ABSTRACT

Predominately amino terminated phosphonamide oligomers and their use as flame retardant additives in polyamides and copolyamides without detracting from melt processability are described herein. Other important properties such as strength, modulus, dyeing and thermal stability are maintained.

14 Claims, No Drawings

FLAME RETARDANT POLYAMIDE COMPOSITIONS

CROSS-REFERENCE TO RELATED APPLICATIONS

This application claims priority to U.S. Provisional Application No. 61/558,296, entitled, "Thermoplastic Polyurethanes with Exceptional Fire Resistance," filed Nov. 10, 2011, which is incorporated herein by reference in its entirety.

GOVERNMENT INTERESTS

Parties to a Joint Research Agreement

Incorporation by Reference of Material Submitted on a Compact Disc

BACKGROUND

Summary of the Invention

The invention comprises predominately amino terminated phosphonamide oligomers combined with a polyamide or copolyamide to provide a flame resistant resin composition. The invention achieves a combination of flame retardancy and processability by melt mixing, without significantly detracting from strength, modulus, dyeing and thermal stability of the unmodified host polyamide.

DESCRIPTION OF DRAWINGS

Not applicable.

DETAILED DESCRIPTION

Before the present compositions and methods are described, it is to be understood that this invention is not limited to the particular processes, compositions, or methodologies described, as these may vary. It is also to be understood that the terminology used in the description is for the purpose of describing the particular versions or embodiments only, and is not intended to limit the scope of the present invention, which will be limited only by the appended claims. Unless defined otherwise, all technical and scientific terms used herein have the same meaning as commonly understood by one of ordinary skill in the art. Although any methods and materials similar or equivalent to those described herein can be used in the practice or testing of embodiments of the present invention, the preferred methods, devices, and materials are now described. All publications mentioned herein are incorporated by reference in their entirety. Nothing herein is to be construed as an admission that the invention is not entitled to antedate such disclosure by virtue of prior invention.

It must also be noted that, as used herein and in the appended claims, the singular forms "a", "an", and "the" include plural reference unless the context clearly dictates otherwise. Thus, for example, reference to "a combustion chamber" is a reference to "one or more combustion chambers" and equivalents thereof known to those skilled in the art, and so forth.

As used herein, the term "about" means plus or minus 10% of the numerical value of the number with which it is being used. Therefore, about 50% means in the range of 45%-55%.

The terms "flame retardant," "flame resistant," "fire resistant," or "fire resistance," as used herein, means that the composition exhibits a limiting oxygen index (LOI) of at least 27. "Flame retardant," "flame resistant," "fire resistant," or "fire resistance," may also refer to the flame reference standard ASTM D6413-99 for textile compositions, flame persistent test NF P 92-504, and similar standards for flame resistant fibers and textiles. Fire resistance may also be tested by measuring the after-burning time in accordance with the UL test (Subject 94). In this test, the tested materials are given classifications of UL-94 V-0, UL-94 V-1 and UL-94 V-2 on the basis of the results obtained with the ten test specimens. Briefly, the criteria for each of these UL-94-V-classifications are as follows:

UL-94 V-0 the total flaming combustion for each specimen after removal of the ignition flame should not exceed 10 seconds and none of the test specimens should release and drips which ignite absorbent cotton wool.

UL-94 V-1: the total flaming combustion for each specimen after removal of the ignition flame should not exceed 30 seconds and none of the test specimens should release any drips which ignite absorbent cotton wool.

UL-94 V-2: the total flaming combustion for each specimen after removal of the ignition flame should not exceed 30 seconds and the test specimens release flaming particles which ignite absorbent cotton wool.

Fire resistance may also be tested by measuring after-burning time. These test methods provide a laboratory test procedure for measuring and comparing the surface flammability of materials when exposed to a prescribed level of radiant heat energy to measure the surface flammability of materials when exposed to fire. The test is conducted using small specimens that are representative, to the extent possible, of the material or assembly being evaluated. The rate at which flames travel along surfaces depends upon the physical and thermal properties of the material, product or assembly under test, the specimen mounting method and orientation, the type and level of fire or heat exposure, the availability of air, and properties of the surrounding enclosure. If different test conditions are substituted or the end-use conditions are changed, it may not always be possible by or from this test to predict changes in the fire-test-response characteristics measured. Therefore, the results are valid only for the fire test exposure conditions described in this procedure.

A number of approaches have been investigated to impart flame retardancy to polyamides and copolyamides with varying degrees of success. In general, it has been extremely challenging to impart flame retardancy to polyamides and copolyamides without detracting from other important properties in particular from melt processability. First, one needs to select a flame retardant additive that is miscible with the polyamides or copolyamides and/or that can be homogeneously dispersed in the polyamide of copolyamide matrix. Secondly, often there is an unacceptable increase in the melt viscosity of the polyamide during processing that is caused by the flame retardant additive. In the worst case, a chemical reaction occurs between the flame retardant and the polyamide, and the composition rapidly hardens and melt processability is lost. In addition to maintaining melt processability it is important that other important properties such as strength, modulus, dye-ability and thermal stability of the host polyamide are not significantly diminished.

Recently phosphinate salts either alone or in combination with nitrogen compounds such as melamine derivatives have been the focus of flame retardant additives. Red phosphorus has also been used as a flame retardant because in can tolerate the high processing temperatures associated with polyamides and copolyamides. In both approaches the amount of additives required to achieve acceptable flame retardant behavior in polyamides is sufficiently high so as to cause an increase in melt viscosity of the composition. In the case of the metal phosphinates and melamine derivatives, they are small non-reactive molecules that can leach out of the resin into the surrounding environment. In the case of red phosphorus, it is highly reactive at elevated temperature and is toxic and dangerous to handle.

Other approaches to imparting flame retardant properties to polyamides have involved the use of phosphorus containing polymers combined with melamine derivatives or polyphosphonamides. Since these approaches use a high molecular weight unreactive polymer, and the loading level required to achieve flame resistance is high, the melt viscosity of the composition is typically increased which is undesirable and limiting.

Thus, there is a need to provide flame retardancy to polyamides and copolyamides without detracting from melt processability, strength, modulus, dyeing, and thermal stability as compared to the unmodified polyamide.

Embodiments of the invention are directed to phosphonamide oligomers that can be combined with known polyamides to produce flame retardant polyamide compositions that overcome toxicity, melt stability, and migration problems associated with metal containing additives while satisfying standardized fire resistance requirements and without detracting from mechanical and processing properties. In other embodiments, the flame retardant compositions may further include one or more additional additives such as, but not limited to, flame retardant additives, fillers, dyes, antioxidants, anti-dripping agents, lubricants, $C_4$ salts such as perfluorobutane sulfonic acid sodium or potassium salts and other additives typically used with polyamides and copolyamides can be used. Further embodiments are directed to methods for preparing the flame retardant polymer mixtures by, for example, melt mixing the phosphonamide oligomers described herein with one or more polyamide.

Embodiments are not limited to particular phosphonamides. Various known phosphonamides can be reformulated to include amino termini and are encompassed by the invention. In particular embodiments, the amino terminated phosphonamides of the invention may have the structure of general Formula I:

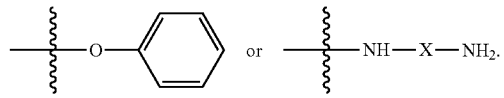

I where R is a $C_1$ to $C_{20}$ alkyl or, optionally substituted, aryl group, X is an aromatic, cycloalkyl, or aliphatic group, n is an integer of from 1 to about 20, and Z is:

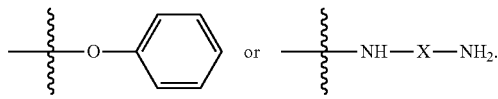

In other embodiments, the phosphonamide oligomers may include compounds of Formula II:

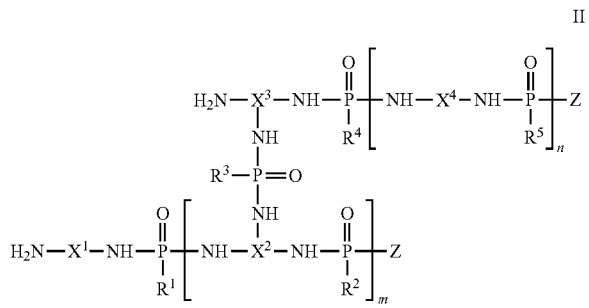

II where $R^{1-5}$ are each individually a $C_1$ to $C_{20}$ alkyl or, optionally substituted, aryl group, $X^{1-4}$ are each individually, an aromatic, cycloalkyl, or aliphatic group, n and m are 0 or an integer of from 1 to about 20, and each Z is, independently:

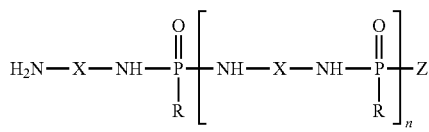

In some embodiments, m and n may each independently be from about 0 to about 10. In other embodiments, may be 0 or an integer of from 1 to about 4, such that the branching, or potential branching is limited, and n may be any integer from 1 to about 20.

In particular embodiments, each —NH—X—NH— provided in Formulae I and II, including the amine containing moieties including $X^{1-4}$, may be derived from an amine containing monomer including all known diamine, triamine, or polyamine containing monomers. In certain embodiments, each —NH—X—NH— may be derived from the same amine containing monomer, and in other embodiments, each —NH—X—NH— may be derived from two or more different amine containing monomers. Exemplary amine containing monomers include alkanediamines, alkanetriamines, arylamines, cycloalkylamines, or any combinations thereof, and in various embodiments, the alkanediamines, alkanetriamines, arylamines, cycloalkylamines may have from about 6 to about 12 or about 20 carbon atoms. In particular embodiments, the alkanediamines, alkanetriamines, arylamines, cycloalkylamines may have from about 6 to about 8 carbon atoms. More specific non-limiting examples of suitable diamines, triamines, and polyamines include m-xylylenediamine, di(4-aminophenyl)methane, di(4-aminocyclohexyl)methane, 2,2-di(4-aminophenyl)propane, 1,4-diaminobutane, 1,3-bis-(aminomethyl)-cyclohexane, 1,4-bis (aminomethyl)-cyclohexane, 2,5-bis(aminomethyl)-bicyclo-[2,2,1]heptane and/or 2,6-bis-(aminomethyl)-bicyclo[2,2,1] heptane, bis-(4-aminocyclohexyl)-derivative of an alkane having from 1 to 6 carbon atoms, and p-xylylene-diamine 2,2-di(4-aminocyclohexyl)propane, and triamine derivatives of these diamines, any mixtures, or combinations thereof. In certain embodiments, —NH—X—NH— may be derived from polyether amine or Jeffamine, which are described herein below.

The weight average molecular weight (Mw) of these phosphonamide oligomer can vary based on the number of monomers incorporated into the polymer chain and can be from about 200 g/mole to about 10,000 g/mole or about 500 g/mole to about 7,500 g/mole in embodiments (all expressed against polystyrene (PS) standards). The phosphonamide oligomer s of various embodiments may include at least 50% of the available end groups include an amine group, and in some embodiments, the phosphonamides may have from about 50% to about 100%, about 60% to about 90%, about 60% to about 80%, or any range between these exemplary ranges amine end groups based on the total number of available end groups.

The phosphonamide oligomers of such embodiments may be prepared by combining an amine containing monomer and a phosphonate monomer and heating this mixture under vacuum. In some embodiments, the reaction mixture may further include a polymerization catalyst such as, for example, magnesium chloride. In general, the vacuum may be sufficient to remove volatile components, such as phenol, produced as the phosphonamide oligomer is made. In some embodiments, the vacuum may be applied in a step wise manner, in which the vacuum is increased and the pressure of the reaction is reduced one or more times, during the polymerization process, and in other embodiments, the pressure may be gradually reduced throughout the polymerization. In still other embodiments, the vacuum may be increased and the pressure reduced both step wise and gradually in the same polymerization method. For example, in some embodiments, the vacuum may be applied to produce an initial pressure of from about 250 mmHg to about 50 mmHg and the pressure may be reduced gradually, in a step wise manner, or both to from about 10 mmHg to about 5 mmHg. In other exemplary embodiments, the initial pressure may be from about 250 mmHg to about 150 mmHg, and this pressure may be reduced to from about 40 mmHg to about 80 mmHg and then reduced again to about 20 mmHg to about 5 mmHg to produce a method with 3 vacuum steps. Other methods may include more than 3 steps, and still other methods may include less than 3 steps, for example, pressure may be gradually reduced throughout polymerization from about 250 mmHg or 150 mmHg to about 10 mmHg or about 5 mmHg.

The temperature of the reaction may be maintained at any temperature at which polymerization may occur. For example, in some embodiments, the reaction temperature may be from about 175° C. to about 300° C., and in other embodiments, the reaction temperature may be from about 200° C. to about 250° C. or 275° C. In some embodiments, a constant reaction temperature may be maintained throughout the polymerization, and in other embodiments, the reaction temperature may change at various times throughout the polymerization reaction. In particular embodiments, the reaction temperature may be increased at steps as the pressure is decreased. For example, in the context of the exemplary embodiments above, the initial reaction temperature may be about 175° C. to about 220° C. when the pressure is from about 250 mmHg to about 150 mmHg. The reaction temperature may be increased to from about 200° C. to about 230° C. when the pressure reduced to from about 40 mmHg to about 80 mmHg, and the reaction temperature may be increased to from about 220° C. to about 275° C. when the pressure is reduced to about 20 mmHg to about 5 mmHg.

The reaction time may be any amount of time necessary to provide sufficient polymerization and may vary with reactants, catalysts, reaction temperatures and pressures, and so on. The skilled artisan may vary the reaction time according to such considerations. In general, the total reaction time may be from about 10 hours to about 40 hours, and in some embodiments, the total reaction time may be from about 15 hours to about 25 hours. The reaction time for various steps or temperature and pressure intervals may also vary, and each step or interval may individually be from about 2 hours to about 20 hours. In certain embodiments, a lower temperature, higher pressure first step or interval may be from about 2 hours to about 6 hours in length, followed by a longer 10 hour to 25 hour step or interval where the temperature is increased and the pressure is reduced. As discussed above, the reaction time for each step or interval may vary and can be determined by the skilled artisan.

In some embodiments, the amine containing monomer may be provided in a molar excess to increase the number of amine end-groups on the phosphonamide oligomers. As discussed above the amine containing monomer may be any diamine, triamine, or polyamine known in the art. In particular embodiments, the amine containing monomer may be provided in a molar excess of at least 10%, and in other embodiments, the amine containing monomer may be provided in a molar excess of from about 10% to about 50%, about 10% to about 30%, or about 10% to about 25%. Without wishing to be bound by theory, when an amine containing monomer is combined with a phosphonic acid diester and is provided in a molar excess of 10%, the resulting oligomeric phosphonamide may have about 5% excess amino end-groups versus phosphonate ester end groups. In still other embodiments, the reaction mixture may include a branching agent, and the ratio of amine to alkyl diarylphosphonate containing monomers may be adjusted to ensure excess amine end-groups in the resulting oligomeric phosphonamide.

In addition to the methods described above, amino terminated phosphonamides can be prepared from the reaction of diamines, triamines, and polyamines, and phosphonic acid dihalides.

In various embodiments, amine containing monomer may be any known diamine, triamine, or polyamine containing monomer. Exemplary amine containing monomers include alkanediamines, alkanetriamines, arylamines, cycloalkylamines, or any combinations thereof, and in various embodiments, the alkanediamines, alkanetriamines, arylamines, cycloalkylamines may have from about 6 to about 12 or about 20 carbon atoms. In particular embodiments, the alkanediamines, alkanetriamines, arylamines, cycloalkylamines may have from about 6 to about 8 carbon atoms. More specific non-limiting examples of suitable diamines, triamines, and polyamines include m-xylylenediamine, di(4-aminophenyl)methane, di(4-aminocyclohexyl)methane, 2,2-di(4-aminophenyl)propane, 1,4-diaminobutane, 1,3-bis-(aminomethyl)-cyclohexane, 1,4-bis(aminomethyl)-cyclohexane, 2,5-bis(aminomethyl)-bicyclo-[2,2,1]heptane and/or 2,6-bis-(aminomethyl)-bicyclo[2,2,1]heptane, bis-(4-aminocyclohexyl)-derivative of an alkane having from 1 to 6 carbon atoms, and p-xylylene-diamine 2,2-di(4-aminocyclohexyl)propane, and triamine derivatives of these diamines, any mixtures, or combinations thereof.

In particular embodiments, the amine containing monomer may be polyether amines such as Jeffamines. Jeffamines are well known in the art and any polyether amine or Jeffamine can be used to prepare the phosphonamide oligomers of the invention. In particular embodiments, the amine containing monomer may be a Jeffamine of the structures provided below.

| Name | Structure | x | Ave Mw |
|------|-----------|---|--------|
| D230<br>D2000 | 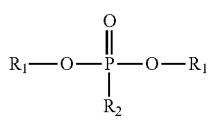 | ~2.5<br>~33 | 230<br>2000 |
| T403 | 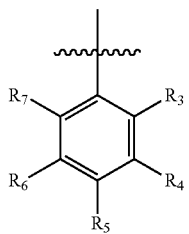 | n = 1<br>(x + y + z) = 5-6<br>R = $CH_2CH_3$ | 440 |

In certain embodiments, the phosphonate containing monomer may be a diaryl alkyl- or arylphosphonate or optionally substituted diaryl alkyl- or arylphosphonate of general formula (I):

$$R_1-O-\underset{\underset{R_2}{|}}{\overset{\overset{O}{\|}}{P}}-O-R_1 \qquad (I)$$

where $R_2$ may be $C_1$-$C_{20}$ alkyl or, optionally substituted, aryl group and $R_1$ may be an aryl group, or a substituted aryl group of formula (II):

(II)

where $R_3$, $R_4$, $R_5$, $R_6$, and $R_7$ may independently be any substituent including but not limited to hydrogen, $C_1$-$C_{20}$ alkyl, aromatic or aryl group, trifluoromethyl, nitro, cyano, halide (F, Cl, Br, I), $C_1$-$C_{20}$ alkyl ether, $C_1$-$C_{20}$ alkyl ester, benzyl halide, benzyl ether, aromatic or aryl ether, or optionally substituted versions of these, and $R_3$, $R_4$, $R_5$, $R_6$, and $R_7$ are essentially unaffected by the reaction. In certain embodiments, the diaryl alkylphosphonate may be diphenyl methylphosphonate.

The amino terminated phosphonamides and oligomeric amino terminated phosphonamides described above may include at least one amino terminus, and in certain embodiments, the amino terminated phosphonamides and oligomeric amino terminated phosphonamides may have two or more amino termini. In some embodiments, the molecular weight of the oligomeric amino terminated phosphonamides may be substantially the same. In other embodiments, the oligomeric amino terminated phosphonamides may be present in a statistical mixture of various molecular weight species. In such statistical mixtures, an amino group is present of both ends of the same molecule, one end of the molecule, or on neither end of different molecules. In particular embodiments, the predominately amino terminated phosphonamide oligomer may include at least 50% of amino end groups related to the total amount of end groups.

The phosphonamide oligomers described herein overcome the problems of toxicity and leaching while satisfying the UL or comparable standardized flame resistance rating performance requirements without detracting from important physical, mechanical and processing properties. This is achieved by formulating a composition of a reactive monomer, oligomer or polymer and an effective amount of an amino terminated phosphonamide oligomer. The amount of the amino terminated phosphonamide may be provided in any appropriate flame retarding amount and can range up to about 50% by weight of the final composition, and in some embodiments, the amount of amino terminated phosphonamide may be from about 10% to about 30%, by weight of the final composition. In some embodiments, the oligomeric amino-terminated phosphonamide can be cured with the host resin, and in other embodiments, the oligomeric amino terminated can be pre-reacted with the host resin.

In particular embodiments, polyamides in the flame retardant polyamide mixtures may be aliphatic or aromatic or aliphatic-aromatic polyamides. The polyamides may be polyhexamethylene adipamide, polyhexamethylene sebacamide, polycaprolactam, and copolyamide 6/66, especially with a proportion of from 5 to 95% by weight of caprolactam units. In other embodiments, the polyamides and copolyamides can be, for example, nylon-4, nylon-6, nylon-6,6, nylon-6,10, nylon-6,9, nylon-6,12, nylon-4,6, nylon-12,12, nylon-11, nylon-12, aromatic polyamides based on m-xylene, diamine and adipic acid; polyamides prepared from hexamethylenediamine and terephthalic acid and/or isophthalic acid. In some embodiments, the polyamides may further include an elastomer such as, for example, poly-2,4,4-trimethylhexamethylene-terephthalamide or poly-m-phenyleneisophthalamide. Block copolymers of the above polyamides with, for example, polyolefins, olefin copolymers, ionomers, chemically bonded or grafted elastomers, or polyethers, polyethylene glycol, polypropylene glycol, or polytetramethylene glycol, or combinations thereof may be used, and in some embodiments, ethylene propylene diene monomer (EPDM) or acrylonitrile butadiene styrene (ABS) can be used to prepare modified polyamides or copolyamides that can be condensed during processing.

Copolyamides can be obtained by copolymerizing two or more of the abovementioned monomers, and mixtures of a number of polyamides in any desired mixing ratio. In particular embodiments, the polyamide can be a partly aromatic copolyamide, such as nylon-6/6T and nylon-6,6/6T, having a triamine content that is less than about 0.5% by weight or less than 0.3% by weight. In some embodiments, the copolyamides may be random copolyamides having randomly arranged monomeric units, and in other embodiments, the copolyamides can be block copolyamides in which the monomeric units are sequentially added such that portions of the block copolyamide are derived from different monomeric units. In particular embodiments, block copolyamides can be derived from polyamides, copolyamides or combinations thereof selected from polyhexamethylene adipamide, polyhexamethylene sebacamide, polycaprolactam, and copolyamide 6/66, nylon-4, nylon-6, nylon-6,6, nylon-6,10, nylon-6, 9, nylon-6,12, nylon-4,6, nylon-12,12, nylon-11, nylon-12, aromatic polyamides based on m-xylene, diamine and adipic acid; polyamides prepared from hexamethylenediamine and terephthalic acid and/or isophthalic acid, and polyolefins, olefin copolymers, ionomers, chemically bonded or grafted elastomers, or polyethers, polyethylene glycol, polypropylene glycol, or polytetramethylene glycol, or combinations thereof.

The amount of the phosphonamide oligomer mixed with the polyamide can be any amount sufficient to provide adequate flame retardancy and acceptable properties. For example, in some embodiments, the amount of predominately amino terminated phosphonamide oligomer mixed with the polyamide can be from about 2% by weight to about 50% by weight or about 3% to about 40%, by weight relative to the host polyamide, and in other embodiments, the amount of predominately amino terminated phosphonamide oligomer mixed with the polyamide can be from about 5% to about 20%, by weight relative to the host resin. In still other embodiments, the flame retardant polyamide compositions of the invention may further include one or more curing agents, additional flame retardant additives, fillers, anti-dripping agents, stabilizers and other additives typically used with polymers.

Flame retardant polyamide formulations include an amount of a predominately amino terminated phosphonamide oligomer sufficient to produce a flame retardant polymer composition will generally meet or exceed the Underwriters Laboratory (UL) or similar standardized fire resistance ratings required for a variety of consumer products without detracting from other important safety, environmental, manufacturing and consumer use requirements. For example, consumer electronics and other consumer products must meet particular fire resistance standards as specified by UL or other standardized criteria. The electronics and products often contain circuit boards, housings or other components or subcomponents that can be comprised of the copolymer, copolymer compositions, filled copolymer, and fiber reinforced copolymer compositions that can include the flame retardant polyamide compositions of embodiments of the invention. The components fabricated from these compositions can meet the V-0 or similar criteria for fire resistance without compromising other properties such as Tg, heat deflection temperature (HDT), and interfacial adhesion. Moreover, the flame retardant polyamide compositions of the invention overcome problems of toxicity and leaching.

Other embodiments of the invention include methods for making the flame retardant polyamides. Such methods generally include the step of melt blending at least one predominately amino terminated phosphonamide oligomer with one or more polyamide. The melt blending may be carried out by any mixing technique, for example, melt mixing may be carried out in a Brabender mixer or extruder. In some embodiments, the methods may include the steps of extruding the mixture after melt blending and pelletizing the resulting material. In other embodiments, the methods may include compressing the melt blended material in rollers to create a film, spincasting a film, or blowmolding a film. In still other embodiments, the methods may include molding the melt blended material into an article of manufacture. Without wishing to be bound by theory, the predominately amino terminated phosphonamide oligomers of the invention undergo a transamidation reaction to some degree and become incorporated into the polyamide or copolyamide backbone during melt blending, thus incorporating the predominately amino terminated oligomer covalently into the matrix of the host polymer.

Still further embodiments of the invention include articles of manufacture prepared from or incorporating the flame retardant polyamides of the invention including, but not limited to free standing films and sheets, fibers, foams, molded articles, coated substrates, adhesives, or fiber reinforced composites. These can subsequently be used in a variety of components that find use in the furnishing, clothing, electronic, automotive, chemical, energy, and other industrial sectors. For example, the flame retardant polyamides of the invention may be incorporated into various consumer goods such as electronics, automotive parts, fabrics used to make clothing or furnishings. In particular embodiments, the flame retardant polyamide described herein can be used in carpet fiber, apparel, upholstery, airbags, tires, conveyor belts, hoses, and the like.

EXAMPLES

Although the present invention has been described in considerable detail with reference to certain preferred embodiments thereof, other versions are possible. Therefore the spirit and scope of the appended claims should not be limited to the description and the preferred versions contained within this specification. Various aspects of the present invention will be illustrated with reference to the following non-limiting examples.

Materials

Jeffamine diamines (D230 and T403) were purchased from Huntsman Petrochemical Corporation. m-Xylene diamine and hexamethylene diamine were purchased from Sigma-Aldrich. Diphenyl methyl phosphonate (DPP) was prepared using methods referred to in U.S. Pat. No. 7,888,534 B2 and U.S. Pat. No. 7,928,259 B2

Methods

GPC: Molecular weight distributions were determined by measuring ~0.5 (w/v) % solutions of polymer in tetrahydrofuran by gel permeation chromatography (GPC) using a refractive index detector. Calibration of the instrument was conducted with linear polystyrene (PS) standards of known molecular weights. The weight average (Mw), number average (Mn) and polydispersity (Mw/Mn), referred to as PD, were evaluated from the chromatograms by using WinGPC software.

DSC: Glass transition temperatures (Tg) were measured using differential scanning calorimetry (DSC). The material was heated at a rate of 10° C./min to 250° C. After keeping the sample at this temperature for 10 minutes, the temperature of the sample was decreased at a rate of 40° C./min to 10° C. The Tg was determined during a second heating cycle (10° C./min to 250° C.) based on the ½ Cp method.

GC-MS: The reaction was monitored by gas chromatography-mass spectroscopy (GC-MS) by analysis of the phenol by-product.

$^1$H-NMR: The amino terminated phosphonamide oligomer was analyzed using nuclear magnetic resonance spectroscopy.

ICP-OES: The % phosphorus was determined using inductively coupled plasma optical emission spectrometry (ICP-OES).

Example 1

Synthesis of Amino Terminated Phosphonamide Oligomer 276.0 g (1.2 mol) Jeffamine D230, 297.8 g (1.2 mol) diphenylmethyl phosphonate (DPP), and 3.05 g (0.03 mol) magnesium chloride were combined in a 1 L round bottom flask and heated to 200° C. while stirring for 14 hrs. Vacuum was gradually lowered to 60 mmHg over 6 hrs, and maintained at 40 mm Hg for 4 hrs, and then lowered to 10 mmHg for 4 hrs. The distillation column was maintained at 115° C. for 14 hrs. The distillate was collected in a flask cooled in ice. After 14 hrs, full vacuum was applied (<0.5 mmHg) and the temperature increased to 240° C. over 2.5 hrs. The product was isolated as a highly viscous liquid (320.6 g). GC-MS analysis of the distillate indicated the total phenol collected was 170.3 g (1.8 mol), residual diamine 23.2 g (0.1 mol) and residual DPP collected was 53.7 g (0.2 mol). Anal. % P, 10.0 wt. %.

Example 2

Synthesis of Amino Terminated Phosphonamide Oligomer 175.0 g (0.39 mol) Jeffamine T403, 124.1 g (0.5 mol) DPP, and 1.24 g (0.013 mol) magnesium chloride were combined in a 500 mL round bottom flask and heated to 200° C. while stirring for 14 hrs. Vacuum was gradually lowered to 25 mmHg over 3 hrs, then to 5 mm Hg for 11 hrs. The distillation column was maintained at 115° C. The distillate was collected in a flask cooled in ice. After 14 hrs, full vacuum was applied (<0.5 mm Hg) for 4.5 hrs at 200° C. The product was isolated as a solid (219.1 g). GC-MS analysis of the distillate indicated the total phenol collected was 72.3 g (0.77 mol), and no residual triamine or DPP was collected. Anal. % P, 7.3 wt. %. 1H-NMR: Aromatic 5H (2.6), aliphatic C—CH$_3$ 16H (10.6) Comparison of aliphatic CH$_3$ protons of triamine versus aromatic protons of DPP and 80% yield of phenol indicates reaction at 2 amine sites resulting in Mn~760.

Example 3

Synthesis of Amino Terminated Phosphonamide Oligomer 84.46 g (0.62 mol) of m-xylene diamine, 153.89 g (0.62 mol) of DPP, and 0.156 g (1.64 mmol) magnesium chloride were combined in a 500 mL round bottom flask and heated to 250° C. while stirring for 14 hrs. Vacuum was gradually lowered to 40 mmHg over 4 hrs, then to 4 mmHg for 6 hrs. After 10 hrs, full vacuum was applied (<0.3 mm Hg) for 4 hrs at 250° C. The distillation column was maintained at 120° C. The distillate was collected in a flask cooled in ice. The product was isolated as a solid (121 g). GC-MS analysis of the distillate indicated the total phenol collected was 112.53 g (1.2 mol), and no residual diamine or DPP was collected. Anal. % P, 12.5 wt. %.

Example 4

Synthesis of Amino Terminated Phosphonamide Oligomer 133.2 g (0.93 mol) of hexamethylene diamine, 229.5 g (0.93 mol) of DPP, and 0.234 g of magnesium chloride were combined in a 500 mL round bottom flask and heated to 208° C. while stirring for 16 hrs. Vacuum was gradually lowered to 40 mmHg over 6 hrs, then to 4 mmHg for 6 hrs. After 12 hrs, full vacuum was applied (<0.3 mm Hg) for 4 hrs at 208° C. The distillation column was maintained at 120° C. The distillate was collected in a flask cooled in ice. The product was isolated as a solid (175 g). GC-MS analysis of the distillate indicated the total phenol collected was 170.0 g (1.81 mol), and no residual diamine or DPP was collected. Anal. % P, 13.2 wt. %.

Example 5

Melt Mixed Compositions

Amino terminated phosphonamide oligomers as prepared in Example 1 to Example 4 were melt blended with a polyamide 6,6 and a polyamide containing 43 wt % glass fibers (Polyram Plustek PA303G43, PA 6,6 GF). Prior to blending, the polyamides and the phosphonamide prepared in EXAMPLE 3 were dried under vacuum in an oven overnight at 65° C. and the additional phosphonamides were dried under vacuum in an oven overnight at 15° C. In a Brabender melt mixer, 40 g of the PA 6,6 was melted at 270° C. for 3 minutes. To the PA melt, 10 g of the amino terminated phosphonamide oligomer with 0.1 g of Irganox B 900 were added and allowed to mix for 5 minutes. The amino terminated phosphonamide oligomers mixed well with the PA 6,6 with no apparent increase in melt viscosity. There was no increase in the torque observed during the processing window (5 min). By visual inspection, the mixture appeared homogenous. The product was isolated as a hard solid material.

Flame Retardancy Testing

The resulting blend was shaped with a compression molding to form test specimen. A specimen vertically clamped at its upper end was burned by application of standard flame to its lower end for 10 seconds. The time required for the test specimen to burn until the fire goes out was measured (the first flame times). Immediately after that, the test specimen was burned again by the application of a standard flame for 10 seconds. The time required for the test specimen to burn until the fire goes out was measured (the second flame times). The measurement was repeated for four test specimens. All specimens of the blends self-extinguished instantly when the flame was removed. A summary of the melt mixing conditions and flame retardancy test result is provided in Table 1.

TABLE 1

Melt Mixing Conditions and Flame Retardancy Testing Results

|  | Example 5A | Example 5B | Example 5C | Example 5D |
|---|---|---|---|---|
| Melt Mixed Formulation | | | | |
| PA 6,6 (g) |  |  | 40 | 40 |
| PA 6,6 GF (g) | 40 | 40 |  |  |
| Irganox B 900 (g) | 0.1 | 0.1 | 0.1 | 0.1 |
| Phosphonamide in Example 1 (g) | 10 |  |  |  |
| Phosphonamide in Example 2 (g) |  | 10 |  |  |
| Phosphonamide in Example 3 (g) |  |  | 10 |  |
| Phosphonamide in Example 4 (g) |  |  |  | 10 |
| wt % P in final formulation | 1.5 | 2.0 | 2.5 | 2.6 |
| Brabender Processing Conditions | | | | |
| Temp (° C.) | 270 | 270 | 270 | 270 |
| Speed (RPM) | 50 | 50 | 50 | 50 |
| PA 6,6 melt time (min) | 3 | 3 | 3 | 3 |
| PA + Phosphonamide mix time (min). | 5 | 5 | 5 | 5 |
| Blend maximum torque (Nm) | | | | |
| Flame Retardancy | | | | |
| Flame time (sec.) | <1 | <1 | <1 | <1 |

Comparative Example 6

Melt Mixed Compositions

Hydroxyl terminated phosphonate polymer and oligomers (FRX Polymers Nofia HM1100, Nofia OL5000 and Nofia OL1001) were melt blended with a polyamide 6,6 (Sigma-Aldrich) and a polyamide containing 43 wt % glass fibers (Polyram Plustek PA303G43, PA 6,6 GF). Prior to blending, the polyamides and the phosphonates were dried under vacuum in an oven overnight at 65 and 80° C., respectively. In a Brabender melt mixer, 40 g of the PA 6,6 was melted at 270° C. for 3 minutes. To the PA melt, 10 g of the phosphonate with 0.1 g of Irganox B 900 were added and allowed to mix for 5 minutes. Nofia OL5000 and Nofia OL1001 (oligomer products) did not mix with the polyamide and phase separation was observed resulting in an inhomogeneous blend. The Nofia HM1100 (polymer product) apparently mixed well with the PA 6,6 with no apparent increase in melt viscosity.

Flame Retardancy Testing

The resulting blend was shaped with a compression mold to form test specimen. A specimen vertically clamped at its upper end was burned by application of standard flame to its lower end for 10 seconds. The time required for the test specimen to burn until the fire goes out was measured (the first flame out time). Immediately after that, the test specimen was burned again by the application of a standard flame for 10 seconds. The time required for the test specimen to burn until the fire goes out was measured (the second flame out time). The measurement was repeated for four test specimens. A summary of the melt mixing conditions and flame retardancy test result is provided in Table 2. The flame out times of all blends ranged from <1 second to 63 seconds indicating an inhomogeneous distribution of the phosphonate polymer in the polyamide matrix as a result of an incompatibility of the phosphonates with the polyamide. Apparently, when specimens were ignited in an area that was rich in phosphonates, a short flame out time was observed indicating the effectiveness of phosphonates as flame retardant additives. However, in some cases, very long flame out times were recorded that can only be explained by a low concentration of phosphonate moieties in the specific part that was ignited. This incompatibility of phosphonates with polyamides was already visually observed when the phosphonate oligomers were mixed with the polyamides as described above. Although this phase separation was not observed when the phosphonate polymer was mixed with the polyamides, still an inhomogeneous mixture was obtained with some areas rich and other areas depleted in phosphonates as evidenced by the large range of flame out times for these blends. These results are very different from the results from Example 5 where all samples showed very short flame out times indicating a homogeneous mixture of the polyamides and the phosphonamides.

TABLE 2

Melt Mixing Conditions

|  | Comparative Example 6A | Comparative Example 6B | Comparative Example 6C1C |
|---|---|---|---|
| Melt Mixed Formulation | | | |
| PA 6,6 (g) |  | 40 | 40 |
| PA 6,6 GF (g) | 40 |  |  |
| Irganox B 900 (g) | 0.1 | 0.1 | 0.1 |
| Nofia HM1100 (g) | 10 |  |  |
| Nofia OL5000 (g) |  | 10 |  |
| Nofia OL1001 (g) |  |  | 10 |
| % P in final formulation | 1.5 | 2.0 | 2.5 |
| Brabender Processing Conditions | | | |
| Temp (° C.) | 270 | 270 | 270 |
| Speed (RPM) | 50 | 50 | 50 |
| PA 6,6 melt time (min) | 3 | 3 | 3 |
| PA + Phosphonate mix time (min). | 5 | 5 | 5 |
| Flame retardancy | | | |
| Flame times (sec.) | <1~20 | <1~55 | <1~63 |

The invention claimed is:

1. A polymer composition comprising at least one phosphonamide oligomer of Formula I:

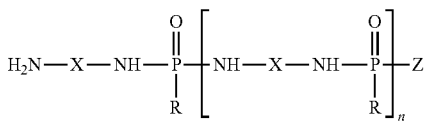

wherein:
R is a $C_1$ to $C_{20}$ alkyl or, optionally substituted aryl group;
X is an aromatic or aliphatic group;
Z is:

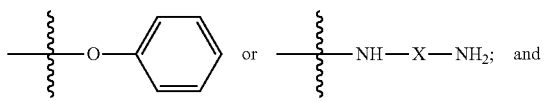

n is an integer of from 1 to about 20; and
one or more polyamides, copolyamides or combinations thereof.

2. The composition of claim 1, wherein at least 50% of available end groups of the phosphonamide oligomer are amine groups.

3. The composition of claim 1, wherein the phosphonamide oligomer comprises a molecular weight of about 200 g/mole to about 10,000 g/mole using polystyrene standards.

4. The composition of claim 1, wherein the composition comprises about 2 wt. % to about 50 wt % phosphonamide oligomer.

5. The composition of claim 1, wherein the one or more polyamides, copolyamides or combinations thereof are selected from the group consisting of polyhexamethylene adipamide, polyhexamethylene sebacamide, polycaprolactam, and copolyamide 6/66, nylon-4, nylon-6, nylon-6,6, nylon-6,10, nylon-6,9, nylon-6,12, nylon-4,6, nylon-12,12, nylon-11, nylon-12, aromatic polyamides based on m-xylene, diamine and adipic acid; polyamides prepared from hexamethylenediamine and terephthalic acid and/or isoterephthalic acid.

6. The composition of claim 1, wherein the one or more polyamides, copolyamides or combinations thereof further comprises monomers derived from ethylene propylene diene monomer (EPDM) or acrylonitrile butadiene styrene (ABS).

7. The composition of claim 1, wherein the composition is a homogeneous composition.

8. The composition of claim 1, further comprising one or more elastomers.

9. The composition of claim 8, wherein the one or more elastomers are selected from the group consisting of poly-2,4,4-trimethylhexamethylene-terephthalamide or poly-m-phenyleneisophthalamide.

10. The composition of claim 1, wherein the one or more polyamides, copolyamides or combinations thereof comprise block copolymers.

11. The composition of claim 10, wherein the block copolymers comprise one or more polyamides, copolyamides or combinations thereof selected from the group consisting of polyhexamethylene adipamide, polyhexamethylene sebacamide, polycaprolactam, and copolyamide 6/66, nylon-4, nylon-6, nylon-6,6, nylon-6,10, nylon-6,9, nylon-6,12, nylon-4,6, nylon-12,12, nylon-11, nylon-12, aromatic polyamides based on m-xylene, diamine and adipic acid; polyamides prepared from hexamethylenediamine and terephthalic acid and/or isoterephthalic acid, and polyolefins, olefin copolymers, ionomers, chemically bonded or grafted elastomers, or polyethers, polyethylene glycol, polypropylene glycol, or polytetramethylene glycol, or combinations thereof.

12. An article of manufacture comprising a polymer composition comprising at least one phosphonamide oligomer of Formula I:

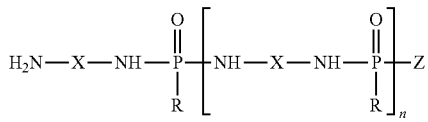

wherein:
R is a $C_1$ to $C_{20}$ alkyl or, optionally substituted aryl group;
X is an aromatic or aliphatic group;
Z is:

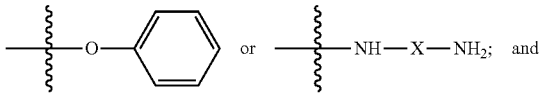

n is an integer of from 1 to about 20; and
one or more polyamides, copolyamides or combinations thereof.

13. The article of manufacture of claim 12, wherein the article is selected from the group consisting of free standing films and sheets, fibers, foams, molded articles, coated substrates, adhesives, and fiber reinforced composites.

14. The article of manufacture of claim 12, wherein the article is selected from electronics, automotive parts, fabrics used to make clothing or furnishings, carpet fiber, apparel, upholstery, airbags, tires, conveyor belts, and hoses.

* * * * *